(12) United States Patent
Naumovski

(10) Patent No.: US 12,405,190 B2
(45) Date of Patent: Sep. 2, 2025

(54) SYSTEM AND METHOD FOR DETECTING AIRBORNE PATHOGENS

(71) Applicant: Steve Naumovski, Dianella (AU)

(72) Inventor: Steve Naumovski, Dianella (AU)

(73) Assignee: Steve Naumovski, Dianella (AU)

( * ) Notice: Subject to any disclaimer, the term of this patent is extended or adjusted under 35 U.S.C. 154(b) by 428 days.

(21) Appl. No.: 17/424,135

(22) PCT Filed: Nov. 30, 2020

(86) PCT No.: PCT/AU2020/051300
§ 371 (c)(1),
(2) Date: Jul. 19, 2021

(87) PCT Pub. No.: WO2021/155422
PCT Pub. Date: Aug. 12, 2021

(65) Prior Publication Data
US 2022/0373436 A1    Nov. 24, 2022

(30) Foreign Application Priority Data
Feb. 4, 2020  (AU) ............... 2020900297

(51) Int. Cl.
*G01N 1/22*    (2006.01)
*C12M 1/26*    (2006.01)
(Continued)

(52) U.S. Cl.
CPC .......... *G01N 1/2273* (2013.01); *C12M 1/261* (2013.01); *G01N 33/0004* (2013.01); *G01N 2001/4038* (2013.01); *G01N 2035/00881* (2013.01)

(58) Field of Classification Search
None
See application file for complete search history.

(56) References Cited

U.S. PATENT DOCUMENTS

2002/0091334 A1*  7/2002  Weber ............... G01N 15/1023
                                                             600/529
2005/0247868 A1   11/2005  Call et al.
(Continued)

FOREIGN PATENT DOCUMENTS

KR    20110128600    11/2011
KR    20150101648     9/2015
(Continued)

OTHER PUBLICATIONS

Hirst J M (1951), An Automated Volumetric Spore Trap, Annals of Applied Biology, 39(2), pp. 257-265 (Year: 1951).*
(Continued)

*Primary Examiner* — Henry H Nguyen
(74) *Attorney, Agent, or Firm* — Ganz Law, PC

(57) ABSTRACT

A system for detecting airborne pathogens includes a pathogen collector having a surface area for engaging with and collecting pathogens; an electrochemical sensor for detecting pathogens on the pathogen collector, the electrochemical sensor comprising an electrode and a reactive substance selected to electrochemically react with the pathogens; and an air-flow generating pump. The system is configured such that the generated air flow moves pathogens in ambient air towards and/or along the surface area of the pathogen collector such that pathogens engage and accumulate on its surface area. The system is further configured such that the reactive substance of the electrochemical sensor electrochemically reacts with the accumulated pathogens. In response to the electrochemical reaction, the electrochemical sensor's electrode detects an electronic signal that indicates the presence of the pathogens.

12 Claims, 2 Drawing Sheets

Figure 1:
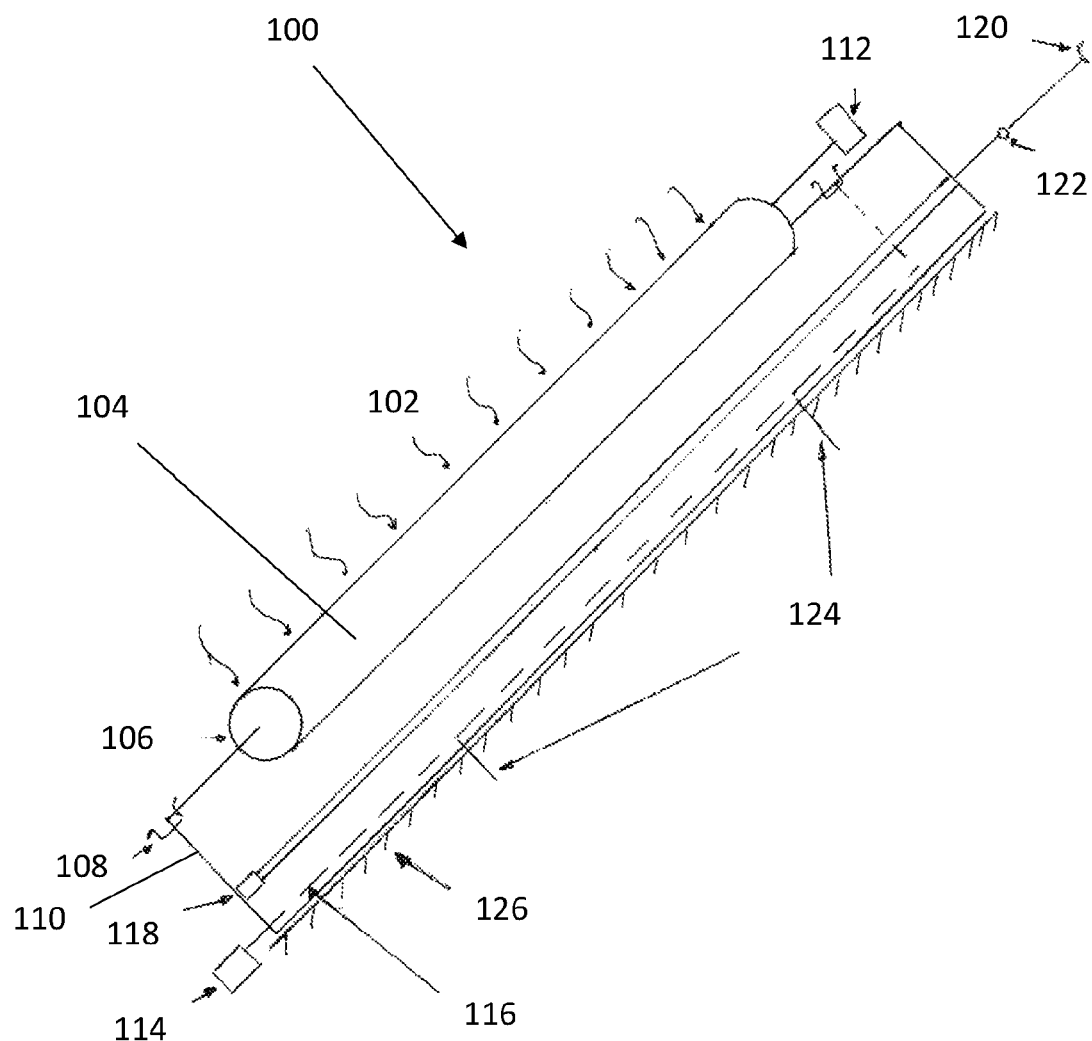

(51) Int. Cl.
*G01N 1/40* (2006.01)
*G01N 33/00* (2006.01)
*G01N 35/00* (2006.01)

(56) References Cited

U.S. PATENT DOCUMENTS

| | | | |
|---|---|---|---|
| 2013/0334042 A1* | 12/2013 | Grieve | C12Q 1/005 |
| | | | 204/403.01 |
| 2014/0017723 A1 | 1/2014 | Hwang et al. | |
| 2015/0010902 A1* | 1/2015 | Takenaka | G01N 33/569 |
| | | | 435/7.1 |
| 2015/0075301 A1* | 3/2015 | Scialo | G01N 15/0612 |
| | | | 73/863.22 |
| 2015/0241401 A1* | 8/2015 | Wu | G01N 35/02 |
| | | | 435/309.1 |
| 2017/0073722 A1* | 3/2017 | Kanhye | G01N 21/6428 |
| 2017/0102349 A1* | 4/2017 | Iyer | C12Y 302/01018 |
| 2018/0100869 A1* | 4/2018 | Niemeyer | B01L 3/545 |

FOREIGN PATENT DOCUMENTS

| | | | | |
|---|---|---|---|---|
| KR | 20160013646 | | 2/2016 | |
| WO | WO-2016080487 A1 | * | 5/2016 | C12M 1/00 |

OTHER PUBLICATIONS

Translation of WO2016080487A1, Kunitomo, Nobuhide, May 26, 2016 (Year: 2016).*
International Search Report and Written Opinion for PCT Application No. PCT/AU2020/051300, mailed Mar. 5, 2021, 7 pages.

* cited by examiner

SYSTEM AND METHOD FOR DETECTING AIRBORNE PATHOGENS

TECHNICAL FIELD

The present invention relates to a system and a method for detecting airborne pathogens. In particular, but not exclusively, the present invention relates to a system and a method for detecting the presence of an airborne virus.

BACKGROUND

Airborne pathogens can become airborne or aerosolised in various ways, such as sneezing or talking, and thereby affect both humans and animals. They are often highly and rapidly transmittable and can have significant impacts on health care and agricultural applications.

Conventional methods of detecting pathogens within ambient air are laboratory based. These methods are typically limited by sample collection and it is not possible to detect airborne pathogens in real-time.

It would therefore be advantageous if at least an embodiment of the present invention overcame this problem or at least provided a workable solution in relation to the detection of airborne pathogens.

Any discussion of documents, acts, materials, devices, articles or the like which have been included in the present specification is not to be taken as an admission that any or all of these matters form part of the prior art base or were common general knowledge in the field relevant to the present invention as it existed before the priority date of each claim of this application.

Throughout the specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Embodiments of the present invention relate to a system for detecting airborne pathogens, the system comprising:
a pathogen collector having a surface area for engaging with pathogens so that at least some pathogens that engage with the pathogen collector accumulate on the surface area of the pathogen collector;
an electrochemical sensor for electrochemically detecting pathogens accumulated on the surface area of the pathogen collector, the electrochemical sensor comprising an electrode and a reactive substance selected to electrochemically react with the pathogens;
a pump for generating an air flow;
wherein the system is configured such that the generated air flow moves pathogens in ambient air towards and/or along the surface area of the pathogen collector such that at least some pathogens can engage and accumulate on the surface area of the pathogen collector; and
wherein the system is further configured such that the reactive substance of the electrochemical sensor electrochemically reacts with the pathogens accumulated on the surface area of the pathogen collector and in response to the electrochemical reaction the electrode of the electrochemical sensor detects an electronic signal being indicative of a presence of the pathogens.

Embodiments of the present invention provide significant advantages. In particular, by generating an air flow that moves airborne pathogens so that the pathogens can interact with the pathogen collector, direct sample collection may not necessarily be required. Moreover, real-time detection of pathogens within ambient air may be enabled. In this way, a decision may be made based on the signal detected by the electrochemical sensor.

In an embodiment, the system may be configured such that a strength of the electronic signal is indicative of a concentration of the pathogens accumulated on the surface area of the pathogens collector.

In an embodiment, the system may be configured to determine the concentration of pathogens per volume, such as per cubic metre or any other suitable predefined volume. In addition, the system may be configured to determine a risk factor using the concentration of pathogens per volume.

In an embodiment, the system may be configured to generate an alarm signal when an electronic signal is detected and/or the concentration of pathogens detected at the electrochemical sensor exceeds a predetermined threshold.

For example, the alarm signal may be a visual signal and the system may comprise a light source that is automatically activated when an electronic signal is detected and/or the detected concentration of pathogens exceeds the predetermined threshold. Additionally or alternatively, the alarm signal may be an audio signal and the system may comprise an electroacoustic transducer that is automatically activated when an electronic signal is detected and/or the detected concentration of pathogens exceeds the predetermined threshold, such as a loudspeaker.

In one embodiment, the system comprises a network interface for communicating information indicative of the electronic signal and/or the generated alarm signal to a computing device. The network interface may facilitate wireless communication to a remote computing device. Exemplary computing devices may include but are not limited to a smartphone, a tablet computer, a personal computer, a laptop computer or a PDA. The signal may be transmitted using any suitable wired or wireless transmission technologies, including but not limited to Wi-Fi, Bluetooth, radio frequency and near field.

In one embodiment, the pathogen collector may have a substantially cylindrical shape. The pathogen collector may have a length in a range between 10 cm and 2 m, in particular between 50 cm and 150 cm, in particular between 80 cm and 120 cm, or approximately 50 cm, 60 cm, 70 cm, 80 cm, 90 cm, 100 cm, 120 cm, 150 cm or 2 m. The pathogen collector may have a diameter in a range between 1 cm and 10 cm, in particular between 3 cm and 6 cm, or approximately 1 cm, 2 cm, 3 cm, 4 cm, 5 cm, 6 cm, 7 cm, 8 cm, 9 cm or 10 cm. However, a person skilled in the art will appreciate that other suitable shapes with suitable surface areas are envisaged. For example, the pathogen collector may be in the form of a relatively flat panel with a square or rectangular surface area.

In a specific example, the pathogen collector may be in the form of a roller that is rotatable about a central axis. In this regard, the system may comprise a motor for rotating the roller.

In an embodiment, a material of the surface area of the pathogen collector comprises one or more of the following materials: metal, rubber, foam rubber (polyurethane or latex), wood. In a specific embodiment, the material of the surface area of the pathogen collector comprises tissue, such as biological tissue. This may, for example, be in the form of artificially created skin that forms the surface area of the pathogen collector.

In one embodiment, the reactive substance of the electrochemical sensor is selected and provided to maximise signal detection indicative of the presence and/or concentration of pathogens accumulated on the surface area of the pathogen collector. In this regard, the reactive substance may be provided on a surface area in close proximity to the pathogen collector and that is of similar size as the surface area of the pathogen collector.

In the example of the pathogen collector being in the form of a rotatable roller, the reactive substance of the electrochemical sensor may be provided on a surface area of similar length as the roller.

In an embodiment, the system may be configured to generate an air flow towards and/or along the surface area of the pathogens collector. In a specific example, the system may comprise an air inlet arranged to draw air into the system. The air inlet may be in the form of a slit that extends substantially parallel to the pathogen collector.

In one embodiment, the system may comprise a mount for mounting the system to a surface area, such as a wall panel or a ceiling. The mount may comprise one or more apertures for receiving suitable fasteners, such as screws and bolts.

In one embodiment, the system may comprise a source of antimicrobial agents to inactivate or destroy airborne pathogens. In this regard, the system may be configured to automatically release an antimicrobial agent, for example, through a spray nozzle.

Embodiments of the present invention relate to a method of detecting airborne pathogens, the method comprising:
  providing a surface area of a pathogen collector, and arranging the pathogen collector so that pathogens in ambient air can engage with the surface area and at least a portion of the pathogens accumulates on the surface area of the pathogen collector;
  generating an air flow such that pathogens in ambient air are moved towards and/or along the surface area of the pathogen collector to engage and accumulate on the surface area;
  providing an electrochemical sensor for electrochemically detecting pathogens accumulated on the surface area of the pathogen collector, the electrochemical sensor comprising an electrode and a reactive substance selected to electrochemically react with the pathogens; and
  detecting an electronic signal at the electrode of the electrochemical sensor in response to an electrochemical reaction between the reactive substance and the pathogens accumulated on the surface area of the pathogen collector, wherein the electronic signal is indicative of the presence of pathogens accumulated on the pathogen collector.

In an embodiment, the method is conducted such that a strength of the electronic signal is indicative of the concentration of pathogens accumulated on the pathogen collector. In this regard, the method may comprise a step of determining a concentration of pathogens per predefined volume.

In an embodiment, the method may comprise a step of generating an alarm signal when an electronic signal is detected and/or the concentration of pathogens detected at the electrochemical sensor exceeds a predetermined threshold. For example, a visual and/or audio signal may be generated.

In a further embodiment, the method may comprise a step of communicating information indicative of the presence and/or concentration of pathogens and/or the generated alarm signal to a computing device, such as wirelessly. In this way, information on whether a pre-determined volume contains a concentration of pathogens can be communicated to a remote computing device where a response action may be initiated.

In an embodiment in which the pathogen collector is in the form of a rotatable roller, the method may comprise rotating the roller while the method of detecting airborne pathogens is conducted.

In an embodiment, the method may comprise repeating at least some of the method steps after a predetermined time interval has lapsed. For example, the method may be conducted to be automatically repeated periodically, or upon request. In this regard, the method may comprise a step of automatically cleaning the pathogen collector from pathogens accumulated on the surface area.

In one embodiment, the method may comprise a step of inactivating or destroying airborne pathogens. In this regard, the method may comprise a step of automatically releasing an antimicrobial agent, for example, through a spray nozzle, when an electronic signal is detected and/or when a concentration of the accumulated pathogens exceeds a predetermined threshold.

It will be appreciated by persons skilled in the art that numerous variations and/or modifications may be made to the invention as shown in the specific embodiments and/or aspects without departing from the spirit or scope of the invention as broadly described. For example, it will be apparent that certain features of the invention can be combined to form further embodiments. The present embodiments and aspects are, therefore, to be considered in all respects as illustrative and not restrictive. Several embodiments are described above with reference to the drawings. These drawings illustrate certain details of specific embodiments that implement the systems and methods and programs of the present invention. However, describing the invention with drawings should not be construed as imposing on the invention any limitations associated with features shown in the drawings.

BRIEF DESCRIPTION OF DRAWINGS

Certain exemplary embodiments of the present invention will now be described, by example only, with reference to the accompanying drawing in which:

FIG. 1 is a schematic representation of a system for detecting airborne pathogens in accordance with an embodiment of the present invention, and FIG. 2 is a flow chart illustrating a method of detecting airborne pathogens in accordance with an embodiment of the present invention.

DESCRIPTION OF EMBODIMENTS

Embodiments of the present invention generally relate to a system and a method for detecting airborne pathogens, such as viruses or bacteria present in ambient air. The system generally comprises a pathogen collector that has a surface area for engaging with pathogens in ambient air. By engaging with the pathogen collector, at least some pathogens will accumulate on the surface area of the pathogen collector. The system further comprises an electrochemical sensor for electrochemically detecting the pathogens that have accumulated on the surface area of the pathogen collector. The electrochemical sensor comprises an electrode and a reactive substance selected to electrochemically react with one or more specific types of pathogens. Furthermore, the system comprises a pump for generating an air flow and the system is configured such that the generated air flow moves pathogens in ambient air towards and/or along the surface area of the pathogen collector such that at least some pathogens can engage and accumulate on the surface area of the pathogen collector. The system is further configured such that the reactive substance of the electrochemical sensor electrochemically reacts with the pathogens accumulated on the surface area of the pathogen collector and in response to the electrochemical reaction the electrode of the electrochemical sensor detects an electronic signal that is indicative of the presence of the pathogens accumulated on the pathogen collector. In some embodiments, a strength of the electronic signal is indicative of the concentration of pathogens accumulated on the pathogen collector. The strength of the electronic signal may be analysed to determine a concentration of one or more types of pathogens in a pre-defined region, such as per cubic metre.

As mentioned in the background section, airborne pathogens can become airborne or aerosolised in various ways and may include viruses or bacteria. Exemplary viruses that the system may detect include but are not limited to respiratory viruses, gastrointestinal viruses, exanthematous viruses, hepatic viruses, cutaneous viruses, haemorrhagic viruses, neurologic viruses or arthropod-borne viruses if present on the pathogen collector.

Conventional methods of detecting pathogens within ambient air are typically laboratory based and are therefore limited by sample collection. As such, it is not possible to detect airborne pathogens in real-time. Embodiments of the present invention aim to overcome this limitation by detecting airborne pathogens in real-time. In this way, once the system detects the presence of a pathogen or the detected concentration exceeds a predetermined threshold, a decision making process may be initiated, such as a process to inactivate the pathogens, evacuating an area or the like.

Possible applications for embodiments of the present invention include private and public spaces, such as houses, factories, hospitals, commercial buildings, airplanes, ships, places of worship, tall buildings, schools, universities, museums, art galleries, pubs and the like.

Referring now to FIG. 1 of the accompanying drawings, there is shown a system 100 for detecting airborne pathogens in accordance with an embodiment of the present invention. In this particular example, the system 100 is configured to detect a virus 102. A person skilled in the art will appreciate that the system 100 may be configured to detect one or more types of viruses or bacteria by suitably selecting the reactive substance of the electrochemical sensor. The material of the surface area of the pathogen collector may further be selected depending on the desired type of pathogen to be detected.

In this particular example, the pathogen collector 104 of the system 100 is in the form of a roller 104 that is rotatable. Thus, the pathogen collector 104 has a cylindrical shape. In this embodiment, the roller 104 has a length of approximately 1 m with a diameter of approximately 5 cm. However, a person skilled in the art will appreciate that other dimensions are envisaged, including but not limited to a length in a range between 10 cm and 2 m, in particular between 50 cm and 150 cm, in particular between 80 cm and 120 cm, or approximately 50 cm, 60 cm, 70 cm, 80 cm, 90 cm, 100 cm, 120 cm, 150 cm or 2 m, and a diameter in a range between 1 cm and 10 cm, in particular between 3 cm and 6 cm, or approximately 1 cm, 2 cm, 3 cm, 4 cm, 5 cm, 6 cm, 7 cm, 8 cm, 9 cm or 10 cm.

Providing a rotatable roller 104 provides the advantage that pathogens that engage and accumulate on the surface area of the pathogen collector 104 can be distributed more evenly. In this way, the signal detected by the electrode of the electrochemical sensor may be improved. However, a person skilled in the art will appreciate that any suitable shapes and sizes are envisaged. For example, the pathogen collector may be in the form of a relatively flat panel with a rectangular surface area.

A material of the surface area of the roller 104 may be selected so that a desired type of pathogen 102 that is moved towards and/or along the surface area of the roller 104 automatically attaches to the surface area. In this way, pathogens 102 accumulate on the surface area so that the electrochemical sensor can detect whether pathogens are present. Exemplary materials include but are not limited to metal, rubber, foam rubber (polyurethane or latex) and wood. In a specific embodiment, the material of the surface area of the pathogen collector comprises tissue, such as biological tissue. This may, for example, be in the form of artificially created skin that forms the surface area of the pathogen collector.

In this example, the roller 104 is rotatable about a central axis 106 at which the roller is attached to a housing 108 of the system 100 via an attachment, in this example clip joints 110. The roller 104 may be attached to the housing in any suitable way. However, providing an attachment so that the roller 104 is removable has the advantage that the roller 104 can be easily replaced and/or cleaned if required.

The roller 104 is further connected to a motor 112 that is configured to rotate the roller 104 about the central axis 106. A rotational speed may be selected to maximise a signal strength detected by the electrochemical sensor. This may be determined using a conventional calibration method. Calibration methods to maximise signal strength are well known in the art and will not further be described herein.

The system 100 further comprises a pump 114 for generating an air flow, in this particular example an air flow that moves pathogens 102 towards and/or along the surface area of the roller 104. Specifically, the system 100 comprises an air inlet 116 in the form of a suction slit 116 that extends substantially parallel to the roller 104 and is arranged such that ambient air including pathogens 102 is directed towards the system 100 to flow around the roller 104 and into the air inlet 116. The inventor of the present invention has found that providing an air flow that directs ambient air towards and/or along the surface area of the pathogen collector 104 has the advantage that a larger volume of air will interact with the surface area of the pathogen collector 104 compared to a system without the generated air flow. In this way, the system 100 may be configured to examine an entire room or space, such as an interior of a plane without the need for collecting a sample. Even more so, airborne pathogens may be detected in substantially real-time which may reduce the risk for the transmission of the detected airborne pathogens as actions to inactivate or destroy the detected pathogens may be immediately initiated.

Referring back to FIG. 1, the system 100 further comprises an electrochemical sensor 118 for electrochemically detecting pathogens 102 accumulated on the surface area of the roller 104. The electrochemical sensor 118 may be any suitable bio sensor that comprises an electrode and a reactive substance selected to electrochemically react with the pathogens 102 to be detected.

In this particular example, the reactive substance of the electrochemical sensor 118 is provided on an open surface of the electrochemical sensor 118 and as close as possible to the surface area of the roller 104 without contacting it. However, a person skilled in the art will appreciate that any suitable distance between the reactive substance and the pathogen collector 104 is envisaged.

In response to the electrochemical reaction between the pathogens 102 that have accumulated on the roller 104 and the reactive substance, the electrode of the electrochemical sensor 118 detects an electronic signal which is indicative of the presence of the pathogens 102. In this example, a strength of the electronic signal is indicative of the concentration of pathogens 102 accumulated on the roller 104. In this way, it can be determined whether any pathogens are present within ambient air.

The system 100 further comprises a controller (not shown), such as a microprocessor, to determine a concentration of pathogens 102 per predefined volume. For example, if the system 100 is mounted on the wall of a closed room, the system 100 may determine a concentration of pathogens 102 within the closed room.

Additionally or alternatively, the controller may be configured to determine whether the detected electronic signal exceeds a predetermined threshold. This may be an indication of the presence of a specific pathogen or of the concentration of the pathogen exceeding a risk threshold. A person skilled in the art will appreciate that any conventional controller is envisaged that is able to process the electronic signal detected by the electrode of the sensor 118. If the controller determines that the detected electronic signal and thereby the measured concentration of pathogens 102 accumulated on the roller 104 exceeds a predetermined threshold, the controller may automatically generate an alarm signal.

In this particular example, the system 100 comprises an electroacoustic transducer 120, for example in the form of a loudspeaker 120, that releases an audio signal when the predetermined threshold of accumulated pathogens 102 has been exceeded. In addition, the system 100 comprises a light source 122, such as an LED light 122, that is automatically activated when the detected concentration of pathogens 102 exceeds the predetermined threshold. In this way, users can be alerted immediately of a potential risk of pathogens 102 within ambient air so that a timely response can be initiated, such as evacuation of a room.

In a further embodiment (not shown), the system also comprises a network interface in communication with the controller so that information indicative of the presence and/or concentration of pathogens and/or the generated alarm signal can be transmitted to a computing device. The network interface may facilitate wireless communication to a remote computing device. Exemplary computing devices may include but are not limited to a smartphone, a tablet computer, a personal computer, a laptop computer or a PDA. A person skilled in the art will appreciate that the information may be transmitted using any suitable wired or wireless transmission technologies, including but not limited to Wi-Fi, Bluetooth, radio frequency and near field.

The system 100 further comprises a mount 124 for mounting the housing 110 of the system 100 to a surface area 126, such as a wall panel or a ceiling.

In one specific embodiment (not shown), the system 100 may comprise a source of antimicrobial agents to inactivate or destroy airborne pathogens. In this regard, the system 100 may be configured to automatically release an antimicrobial agent, for example, through a spray nozzle.

Figure 2:
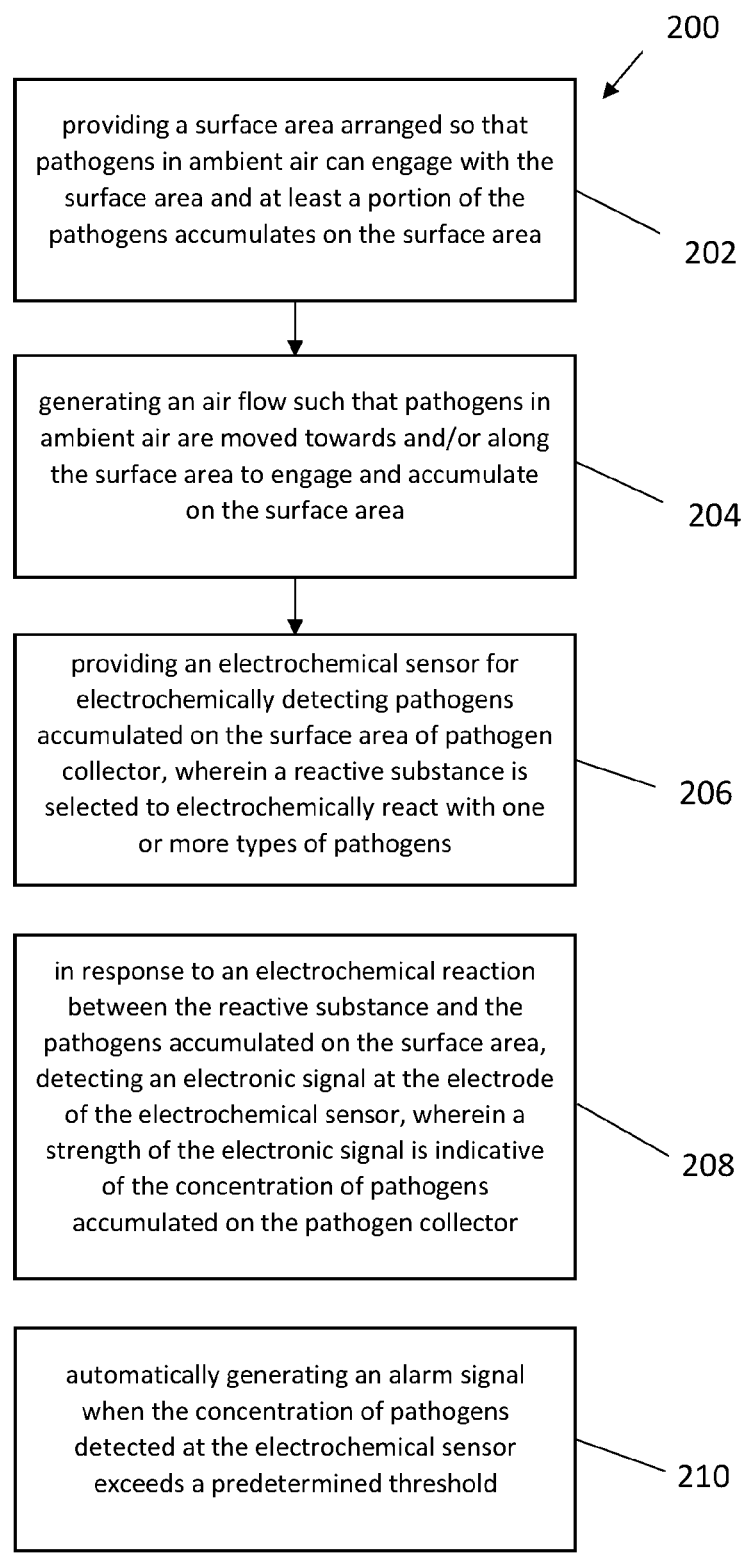

Referring now to FIG. 2, there is shown a flow chart illustrating a method 200 of detecting airborne pathogens in accordance with an embodiment of the present invention. The method 200 comprises a step 202 of providing a pathogen collector with a surface area and arranging the surface area so that pathogens in ambient air can engage with the surface area and at least some pathogens accumulate on the surface area. The pathogen collector may be in the form of a roller as shown in FIG. 1. However, a person skilled in the art will appreciate that any suitable pathogen collectors with surface areas for interacting with airborne pathogens are envisaged.

The method 200 further comprises a step 204 of generating an air flow such that pathogens in ambient air are moved towards and/or along the surface area of the pathogen collector to engage and accumulate on the surface area.

In a further step 206 an electrochemical sensor is provided for electrochemically detecting pathogens accumulated on the surface area of the pathogen collector. The electrochemical sensor may be a conventional bio sensor that comprises an electrode and a reactive substance selected to electrochemically react with one or more types of pathogens, such as a specific virus. In response to an electrochemical reaction between the reactive substance and the pathogens accumulated on the surface area of the pathogen collector, the method 200 comprises a step 208 of detecting an electronic signal at the electrode of the electrochemical sensor, wherein a strength of the electronic signal is indicative of the concentration of pathogens accumulated on the pathogen collector.

In this particular embodiment, the method further comprises 210 automatically generating an alarm signal when the concentration of pathogens detected at the electrochemical sensor exceeds a predetermined threshold. The generated alarm signal may be any suitable signal, such as a visual signal, an audio signal or a signal communicated to a computing device.

In some embodiments, the method 200 may further comprise automatically cleaning the surface area of the pathogen collector to remove the accumulated pathogens. Method steps 202-208 may then be repeated. This may be done periodically or upon request.

In a specific example, the method 200 may comprise a step of inactivating or destroying airborne pathogens. This step may be performed automatically once the predetermined threshold of detected concentration is exceeded. Inactivating or destroying airborne pathogens may comprise releasing an antimicrobial agent, for example, through a spray nozzle.

It will be appreciated by persons skilled in the art that numerous variations and/or modifications may be made to the invention as shown in the specific embodiments and/or aspects without departing from the spirit or scope of the invention as broadly described. For example, it will be apparent that certain features of the invention can be combined to form further embodiments. The present embodiments and aspects are, therefore, to be considered in all respects as illustrative and not restrictive. Several embodiments are described above with reference to the drawings. These drawings illustrate certain details of specific embodiments that implement the systems and methods and programs of the present invention. However, describing the invention with drawings should not be construed as imposing on the invention any limitations associated with features shown in the drawings.

The invention claimed is:

1. A system for detecting airborne pathogens, the system comprising:
 a pathogen collector having a cylindrical body defining a longitudinal central axis and defining a curved surface area for engaging with the airborne pathogens so that at least a portion of the pathogens that engages with the pathogen collector accumulates on the curved surface area of the pathogen collector;

a motor connected to the cylindrical body of the pathogen collector and configured to rotate the cylindrical body about the longitudinal axis;

an electrochemical sensor configured and positioned to electrochemically detect the at least a portion of the pathogens accumulated on the curved surface area of the pathogen collector, the electrochemical sensor comprising an electrode and a reactive substance selected to electrochemically react with the at least a portion of the pathogens accumulated on the curved surface area of the cylindrical body of pathogen collector;

a pump for generating an air flow;

the cylindrical body of the pathogen collector rotates about the longitudinal central axis;

the airborne pathogens engage with the curved surface area while the cylindrical body of the pathogen collector rotates so that the at least a portion of the pathogens automatically attach to the curved surface area thereby accumulating on the curved surface area of the cylindrical body of the pathogen collector; and the air flow is generated by the pump that moves the airborne pathogens towards and/or along the curved surface area of the rotating cylindrical body of the pathogen collector; and the reactive substance of the electrochemical sensor electrochemically reacts with the at least a portion of the pathogens accumulated on the curved surface area of the rotating cylindrical body of the pathogen collector;

wherein in response to the electrochemical reaction, the electrode of the electrochemical sensor detects an electronic signal, the electronic signal being indicative of a presence of the at least a portion of the pathogens accumulated on the curved surface area of the rotating cylindrical body of the pathogen collector.

2. The system of claim 1, wherein a strength of the electronic signal is indicative of a concentration of the at least a portion of the pathogens accumulated on the pathogen collector and the system is further configured to determine the concentration of the at least a portion of pathogens per volume.

3. The system of claim 1, being configured to detect the airborne pathogens in substantially real-time.

4. The system of claim 2, being configured to automatically generate an alarm signal when the concentration of the at least a portion of the pathogens accumulated on the pathogen collector detected at the electrochemical sensor exceeds a predetermined threshold.

5. The system of claim 4, wherein the alarm signal is a visual signal and the system comprises a light source that is automatically activated when the detected concentration of the at least a portion of the pathogens exceeds the predetermined threshold.

6. The system of claim 4, wherein the alarm signal is an audio signal and the system comprises an electroacoustic transducer that is automatically activated when the detected concentration of the at least a portion of the pathogens exceeds the predetermined threshold.

7. The system of claim 4, wherein the system comprises a network interface for communicating the electronic signal and/or the generated alarm signal to a computing device, and wherein the network interface facilitates wireless communication to the computing device.

8. The system of claim 1, wherein a material of the surface area of the pathogen collector comprises one or more of: metal, rubber, foam rubber, wood and biological tissue.

9. The system of claim 1, wherein the reactive substance of the electrochemical sensor is selected and shaped to maximize detection of the at least a portion of the pathogens accumulated on the pathogen collector.

10. The system of claim 1, wherein the system comprises an air inlet and the pump is configured to draw ambient air into the air inlet in a way to generate the air flow towards and/or along the surface area of the pathogens collector.

11. The system of claim 10, wherein the air inlet is configured as a slit.

12. The system of claim 1, comprising a mount for mounting the system to a wall or ceiling surface area.

* * * * *